US006962800B2

(12) United States Patent
Kiy et al.

(10) Patent No.: US 6,962,800 B2
(45) Date of Patent: Nov. 8, 2005

(54) EXPRESSION OF RECOMBINANT HUMAN PROTEINS IN TETRAHYMENA

(75) Inventors: Thomas Kiy, Frankfurt am Main (DE); Matthias Rüsing, Köln (DE)

(73) Assignee: Nutrinova Nutrition Specialties & Food Ingredients GmbH (DE)

( * ) Notice: Subject to any disclaimer, the term of this patent is extended or adjusted under 35 U.S.C. 154(b) by 0 days.

(21) Appl. No.: 10/395,433

(22) Filed: Mar. 24, 2003

(65) Prior Publication Data

US 2003/0219869 A1 Nov. 27, 2003

(30) Foreign Application Priority Data

Mar. 30, 2002 (DE) ......................................... 102 14 413

(51) Int. Cl.$^7$ ............................................... C12P 21/06
(52) U.S. Cl. ..................... 435/69.1; 435/69.1; 435/7.1; 435/252.3; 435/320.1; 435/233; 530/350; 530/300; 536/23.1; 514/2
(58) Field of Search ............................... 435/7.1, 69.1, 435/252.3, 320.1, 233; 530/350, 300; 536/23.1; 514/2

(56) References Cited

FOREIGN PATENT DOCUMENTS

| WO | WO 00/46381 | * | 8/2000 |
| WO | WO 00/58483 | | 10/2000 |

OTHER PUBLICATIONS

Gaertig et al., Nature Biotechnology, vol. 17, pp. 462–465, May 1999.*
Glick, et al, "Microbial Production of Therapeutic Agents," Molecular Biotechnology, Chapter 10, ASM Press (Washington, DC), p. 227–252, (1998).
Ashford, et al, "Protein glycosylation," Post–translational Process—A Practical Approach, Chapter 4, Oxford University Press, p. 135–174.
Glick, et al, "Recombinant Protein Production in Eukaryotic Cells," Molecular Biotechnoloby, Chapter 7, ASM Press (Washington, DC), p. 145–169.
Castillo, "Organism Selection," Biopress Technology, Chapter 2, XOMA Corporation (Berkeley, CA), p. 13–45.
Geisse, et al, "Eukaryotic Expression Systems: A Comparison," Protein Expression and Purification 8, Academic Press Inc., p. 271–282, (1996).
Verma, et al, "Antibody engineering: Comparison of bacterial, yeast, insect and mammalian expression systems," J. Immunological Methods, Elsevier, p. 165–181, (1998).
Moremen, et al, "Glycosidases of the asparagine–linked oligosaccharide processing pathway," Glycobiology, vol. 4, Oxford University Press, p 113–125, (1994).
Tuite, et al, "Expressing cloned genes in the yeasts *Saccharomyces cerevisiae* and *Pichia pastoris*," Protein Expression–A Practical Approach, Oxford University Press, Chap. 3, (1999).

Jenkins, et al, "Getting th glycosylation right: Implications for the biotechnology industry," Nature Biotechnology, vol. 14, p. 175–981, (1996).
Henderson's Dictionary of Biological Terms, 10th Edition, Longman Scientific & Technical (Essex, England), p. 438, (1989).
Handbook of Protoctista, An Introduction to Physology, Cambridge University Press, (1995).
Kiy, et al, "Continuous high–cell–density fermentation of the ciliated protozoon Tetrahymena in a perfused bioreactor," Applied Microbiology and Biotechnology, p. 141–146, (1992).
Taniguchi, et al, "Carbohydrates of Lysosomal Enzymes Secreted by *Tetrahymena pyriformis*\*, " Journal of BIological Chemistry, vol. 260, p. 13941–13946, (1985).
Bruns, et al, "Biolistic Transformation of Macro– and Micronuclei," Methods in Cell Biology, vol. 62, Chapter 27, Academic Press, p. 501–512, (1999).
Gaertig, et al, "Methods in Cell Biology," vol. 62, Academic Press, p. 486–500, (1999).
Hai, et al, Methods in Cell Biology, vol. 62, Academic Press, p. 514–531, (1999).
Gaertig, et al, "Surface display of a parasite antigen in the ciliate *Tetrahymena thermophila*," Nature Biotecyhnology, vol. 17, p. 462–465, (May 1999).
Cassidy–Hanley, et al, "Germline and Somatic Transformation of Mating *Tetrahymena thermophila*," Genetics 146, p. 135–147, (1997).
Yao, et al, "Transformation of Tetrahymena to Cycloheximide resistance with a ribosomal protein gene through sequence replacement," Proc. Natl. Acad. Sci., vol. 88, p. 9493–9497, (1991).
Kahn, et al, "Transformation of *Tetrahymena thermophila* by microinjection of a foreign gene," Proc. Natl. Acad. Sci., vol. 90, p. 9295–9299, (Oct. 1993).
Gaertig, et al, "Electroporation–mediated replacdement of a positively and negatively selectable B–tubulin gene in *Tetrahymena thermophila*," Proc. Natl. Acad. Sci., vol. 91, p. 4549–4553, (May 1994).
Boileau, et al, "Transformation of *Paramecium tetraurelia* by Electroporation or Particle Bombardment," J. Euk. Microbiol, p. 56–65, (1999).

(Continued)

*Primary Examiner*—Jon Weber
*Assistant Examiner*—Hope A. Robinson
(74) *Attorney, Agent, or Firm*—Robert H. Hammer, III, P.C.

(57) ABSTRACT

The present invention concerns a method for production of recombinant human proteins, in which *Tetrahymena* cells are transformed with recombinant DNA containing at least one functional gene that codes for a human protein, the recombinant *Tetrahymena* cells are cultured, in which the gene that codes for a human protein is expressed and the proteins are then isolated. The present invention also concerns a corresponding method, in which the gene that codes for a human protein contains a human leader sequence that leads to secretion of the expressed protein.

14 Claims, 2 Drawing Sheets

OTHER PUBLICATIONS

Kelly, "Genetic Transformation of Parasitic Protozoa," Advances In Parasitology, vol. 39, Academic Press, p. 227–270, (1997).

Manstein, et al, "Cloning vectors for the production of proteins in *Dictyostelium discoideum*," Gene. 162, p. 129–134, (1995).

Jung, et al, "The production of recombinant glycoproteins with special reference to simple eukaryotes including *Dictyostelium discoideum*," Biotechnol. Appl. Biochem 25, p. 3–8, (1997).

Hall, et al, Expression of a foreign gene in *CHlamydomonas reinhardtii*, Gene. 124, p. 75–81, (1993).

Schiedlmeier, et al, "Nuclear transformation of Volvox carteri," Proc. Natl. Acad. Sci., vol. 91, p. 5080–5084, (May 1994).

ten Lohuis, et al, "Genetic transformation of dinoflagellates (Amphidinium and Symbiodinium): expression of GUS in microlagae using heterologous promoter constructs," Plant Journal, p. 427–435, (1998).

Dunahay, et al, "Genetic Transformation Of The Diatoms *Cyclotella Cryptica* And *Navicula Saprophila*," J. Phycol. 31, p. 1004–1012, (1995).

Benson, et al, "GenBank," Nucleic Acids Research, vol. 28, No. 1, Oxford University Press, p. 15–18, (2000).

Wuitschick, et al, "Analysis of Genomic G+C Content, Condon Usage, Initiator Condon Context and Translation Termination Sites in *Tetrahymena thermophila*," J. Eukaryot. Microbiol., p. 239–247, (1999).

\* cited by examiner

SEQUENCE LISTING

<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: primer_bind

<400> SEQUENCE: 1
ggcacaatgc attgggtaac ctttattagc                30

<210> SEQ ID NO 2

-continued

```
<211> LENGTH: 34
<212> TYPE: DNA
<213> ORGANISM: Artificial Sequence
<220> FEATURE:
<223> OTHER INFORMATION: primer_bind

<400> SEQUENCE: 2
aaatgggatc ctcataagcc taaggcagct tgac                                    34

<210> SEQ ID NO 3
<211> LENGTH: 30
<212> TYPE: DNA
<213> ORGANISM: Artificial Sequence
<220> FEATURE:
<223> OTHER INFORMATION: primer_bind

<400> SEQUENCE: 3
aaaaataaaa aagtttgaaa aaaaaccttc                                         30

<210> SEQ ID NO 4
<211> LENGTH: 22
<212> TYPE: DNA
<213> ORGANISM: Artificial Sequence
<220> FEATURE:
<223> OTHER INFORMATION: primer_bind

<400> SEQUENCE: 4
gtttagctga ccgattcagt tc                                                 22

<210> SEQ ID NO 5
<211> LENGTH: 54
<212> TYPE: DNA
<213> ORGANISM: Homo sapiens

<400> SEQUENCE: 5
atgaagtggg taacctttat ttccttctct tttctcttta gctcggctta ttcc              54

<210> SEQ ID NO 6
<211> LENGTH: 18
<212> TYPE: PRT
<213> ORGANISM: Homo sapiens

<400> SEQUENCE: 6

Met Lys Trp Val Thr Phe Ile Ser Leu Leu Phe Leu Phe Ser Ser Ala
1               5                   10                  15
Tyr Ser

<210> SEQ ID NO 7
<211> LENGTH: 18
<212> TYPE: DNA
<213> ORGANISM: Homo sapiens

<400> SEQUENCE: 7
aggggtgtgt ttcgtcga                                                      18

<210> SEQ ID NO 8
<211> LENGTH: 6
<212> TYPE: PRT
<213> ORGANISM: Homo sapiens

<400> SEQUENCE: 8

Arg Gly Val Phe Arg Arg
1               5
```

EXPRESSION OF RECOMBINANT HUMAN PROTEINS IN TETRAHYMENA

This application claims priority under 35 U.S.C. 119 (a–d) to German document number 102 14 413.3 file on Mar. 30, 2002.

The present invention concerns recombinant expression of human proteins in *Tetrahymena*.

Production of recombinant proteins by heterologous protein expression represents an alternative to recovery of proteins from natural sources. Natural sources for proteins, for example, as pharmaceuticals, are often limited, very expensive to purify or simply not available. Because of the hazard of toxic or especially infectious contaminants, they can also be very problematical. Biotechnology and genetic engineering, on the other hand, now make possible economical and safe production of an entire series of proteins in sufficient amount by heterologous expression for a wide variety of applications: for example, antibodies (for diagnosis, passive immunization and research), hormones (like insulin, erythropoietin (EPO), interleukins, etc. for therapeutic use), enzymes (for example, in use in food technology, diagnosis, research), blood factors (for treatment of hemophilia), vaccines, etc. (Glick & Pasternak 1998, Molecular Biotechnology, ASM Press, Washington, D.C., Chapter 10: 227–252).

Human proteins for medical application must be identical to the natural protein in biochemical, biophysical and functional properties. During recombinant production of such proteins by heterologous gene expression, it is then kept in mind that, in contrast to bacteria, there are an entire series of post-translational protein modifications in eukaryotic cells, for example, formation of disulfide bridges, proteolytic cleavage of precursor proteins, modifications of amino acid residues, like phosphorylation, acetylation, acylation, sulfatization, carboxylation, myristylation, palmitylation, and especially glycosylations. In addition, proteins in eukaryotic cells are often only brought to the correct three-dimensional structure by a complex mechanism with participation of chaperones. These modifications play a very important role with respect to specific structural and functional properties of proteins, like activity of enzymes, specificity (receptor binding, cell recognition), folding, solubility, etc. of the proteins (Ashford & Platt 1998, in: Post-translational Processing—A Practical Approach Ed. Higgins & Hames, Oxford University Press, Chapter 4: 135–174; Glick & Pasternak 1998, Molecular Biotechnology, ASM Press, Washington D.C., Chapter 7: 145–169).

Modifications deviating from the natural structure can lead to inactivation of the proteins or possess high allergenic potential.

Thus, production of human serum albumin (HSA) in bacteria often leads to incorrectly folded, insoluble proteins, since the required chaperones are missing and the disulfide bridge is not correctly formed. As an alternative to production of natural HSA from human donor blood, various eukaryotic production systems are therefore being developed to produce recombinant HSA. The spectrum extends from expression in plants via fungi to transgenic animals or mammalian cell cultures.

Although an entire series of bacterial and eukaryotic expression systems are established for production of recombinant proteins, there is no universal system that covers the entire spectrum of (especially in eukaryotic proteins) possible protein modifications and would therefore be universally employable (Castillo 1995, Bioprocess Technology 21: 13–45, Geise et al. 1996, Prot. Expr. Purif. 8: 271–282; Verma et al. 1998 J. Immunological Methods 216: 165–181; Glick & Pasternak 1998, Molecular Biotechnology ASM Press, Washington, D.C., Chapter 7: 145–169). However, it is also extremely problematical that some of the frequently used systems lead to unusual and sometimes undesired post-translational protein modifications. Recombinant expressed proteins from yeasts are sometimes glycosylated extremely strongly with mannose residues (see FIG. 1: Protein glycosylation). These so-called "high-mannose" structures from yeasts consist of about 8–50 mannose residues and therefore differ significantly from the mannose-rich glycoprotein structures from mammal cells, which have a maximum of 5–9 mannose residues (Moreman et al. 1994, Glycobiology 4(2): 113–125). These yeast-typical mannose structures are strong allergens and are therefore very problematical in production of recombinant glycoproteins for therapeutic use (Tuite et al. 1999, in Protein Expression—A Practical Approach, Ed. Higgins & Hames, Oxford University Press, Chapter 3: especially page 76). In addition, no hybrid or complex glycoprotein structures can be formed in yeasts, which further constrains their use as an expression system. Plants that have recently been increasingly discussed as production systems for recombinant proteins and are being used for this purpose, on the other hand, have xyloses on the glycoprotein structures, instead of the sialic acid typical for mammals (Ashford & Platt, see above). Xyloses and the $\alpha$-1, 3-linked fucoses detected in plants can represent an allergic risk and are therefore also problematical (Jenkins et al. 1996, Nature Biotech. 14: 975–981).

Consequently, there is a significant demand for new eukaryotic expression systems, especially as an alternative for the very cost-intensive and demanding production of recombinant proteins by mammal culture cells.

Such a system would ideally meet the following requirements:

1) Selection markers and regulative DNA elements (like transcription and translation signals, etc.) must be available.

2) The expression system should have the important eukaryotic post-translational protein modifications, but not produce allergens for humans.

3) Production of recombinant proteins should be as simple and economical as possible, for example, by fermentation of the cells or organisms on a production scale (which can amount to several 1000 liters) on simple media and simple workup of the products. The possibility of secretion of the expressed proteins by the cells would be extremely advantageous for the latter. In this way, separation of the cells from the product-containing culture supernatant is easily possible, and the extent of contaminants to be separated during workup of the product is substantially reduced if cell digestion can be entirely dispensed with.

Protozoans or protists (for definition, see Henderson's Dictionary of Biological Terms, 10$^{th}$ Edition 1989, Eleanor Lawrence, Longman Scientific & Technical, England or Margulis et al. (Editors) 1990. Handbook of Protoctista, Jones & Bartlett, Boston; van den Hoek et al. 1995, Algae—An Introduction to Phycology, Cambridge University Press) might be an interesting alternative as expression systems to the already established eukaryotic expression systems, like yeast, mammal or insect culture cells. These organisms are a very heterogeneous group of eukaryotic, generally unicellular microorganisms. They have the typical compartmentalization and differentiation of eukaryotic cells. Some are relatively closely related to higher eukaryotes, but, on the other hand, are sometimes similar in culturing and growth to yeasts or even bacteria and can be fermented relatively easily at high cell density on simple media on a large scale.

Methods for transformation and heterologous protein expression have been described for a few protists or protozoans. Different attempts at transformation and expression of recombinant proteins have been made, especially in parasitic protozoans, like *Trypanosoma, Leishmania, Plasmodium* and others (Beverly 2000, WO 00/58483). A review is provided by Kelly (1997, Adv. in Parasitol., Vol. 39, 227–270). The possibility of heterologous protein expression was also demonstrated in a number of additional protists (eukaryotic microorganisms), for example, in the slime mold *Dictyostelium discoideum* (Manstein et al. 1995, Gene 162: 129–134, Jung and Williams 1997, Biotechnol. Appl. Biochem. 25: 3–8), in ciliates, like *Paramecium* (Boileau et al. 1999, J. Eukaryot. Microbiol. 46: 55–65) and *Tetrahymena* (Gaertig et al. 1999, Nature Biotech. 17: 462–465, WO 00/46381). Proteins could also be heterologously expressed in photoautotrophic protists, the microalgae. Here we can mention *Chlamydomonas* (Hall et al. 1993, Gene 124: 75–81), Volvox (Schiedlmeier et al. 1994, PNAS 91: 5080–5084), dinoflagellates (ten Lohuis & Miller 1998, Plant Journal 13: 427–435) and diatoms (Dunahay et al. 1995, J. Phycol. 31: 1004–1012). In most cases, however, only simple resistance markers or non-human selection markers were expressed. A special challenge, on the other hand, is production of human proteins as identical as possible to natural ones in non-mammalian cells, especially if glycosylated proteins are involved, like EPO.

Among the ciliates, *Tetrahymena* is a non-pathogenic, unicellular, eukaryotic microorganism that is relatively closely related to the higher eukaryotes and has the cell differentiations typical for them. Although *Tetrahymena* is a true, complexly differentiated eukaryote, it is more similar in culturing and growth properties to the simple yeast or bacteria and can be fermented readily on relatively inexpensive skim milk media on a large scale. Under optimal conditions, the generation time is about 1.5–3 and very high cell densities ($2.2 \times 10^7$ cells/mL, corresponding to 48 g/L dry weight) can be achieved (Kiy and Tiedke 1992, Appl. Microbiol. Biotechnol. 37: 576–579; Kiy and Tiedke 1992, Appl. Microbiol. Biotechnol. 38: 141–146). Because of this, *Tetrahymena* is very interesting for fermentative production of recombinant proteins on a large scale and much more advantageous than, say, mammal cells.

To draw conclusions concerning the glycosylation pattern of proteins produced by *Tetrahymena*, protein samples (from the culture medium of *Tetrahymena* cultures) were investigated by means of lectin blots before or after digestion with peptide:N-glycosidase F (PNGase F) (methods according to Ashfort & Platt, 1991, see above). The N-glycans were also isolated in sequence with the FACE technology (Glyko Inc.).

Investigations by lectin blots show that some proteins of the microsomal or media fraction are N-glycosylated. N-glycans with terminal mannodisaccharides could be detected in both fractions (PNGase F sensitive binding of lectin GNA). These are N-glycans of the mannose-rich type. Additional PNGase F sensitive lectin bonds were not detected, so that the occurrence of terminal fucose (lectin AAA), galactose (RCA, DSA) and N-acetyl glucosamine residues (DSA, GWA) is unlikely in the N-glycans. The found strong glycosylation of the media proteins is not attributed to contamination by the employed medium, since corresponding controls revealed no lectin binding. Proteins secreted by *Tetrahymena* are therefore involved.

Four of the N-glycoside oligosaccharides were isolated in sequence. The following structures were involved: Man5GleNAc2, Man4GlcNAc2, Man3GlcNAc2 and Man2GlcNAc2. These are partial structures of mannose-rich N-glycoside chains, as also detected by Taniguchi et al. (J. Biol. Chem. 260, 13941–13946 (1985)) for *Tetrahymena pyriformis*. Indications of complex or hybrid N-glycoside sugar chains were not found. The results of the lectin blot were therefore confirmed.

*Tetrahymena* therefore exhibit glycosylations of the simple base type (see FIG. 1). Indications for O-glycoside chains on secreted proteins were entirely absent. Relative to other expression systems, *Tetrahymena* therefore possess a significant advantage: the sugar structures are much more similar to the N-glycoside structures of mammal cells than, say, in yeasts (mannose-rich with much more mannose residues and unusual structure) and insects and plants (occurrence of xylose). For some applications, the simple glycosylation type of *Tetrahymena* could also have advantages relative to mammal cell cultures that generally produced complex N-glycoside sugar structures that often strongly influence the biological activity of the protein (for example, clearing rate, etc.) and hamper production (see, for example, erythropoietin production, 80% false glycosylation). *Tetrahymena* is therefore particularly suited for expression of glycosylated proteins, like erythropoietin (EPO).

Transformation of *Tetrahymena* can be achieved by microinjection, electroporation or microparticle bombardment. A number of vectors, promoters, etc. are available for this. Selection of the transformants occurs by means of a resistance marker. *Tetrahymena*, for example, was successfully transformed with an rDNA vector (selection by a paromycin-resistance mutation of rRNA (Tondravi et al. 1986, PNAS 83:4396; Yu et al. 1989, PNAS 86: 8487–8491). In subsequent transformation experiments, cycloheximide or neomycin resistance were successfully expressed in *Tetrahymena* (Yao et al. 1991, PNAS 88:9493–9497; Kahn et al. 1993, PNAS 90: 9295–9299). In addition to these marker genes, Gaertig et al. (1999, Nature Biotech. 17: 462–465) successfully expressed a recombinant fish parasite antigen (from a ciliate) in *Tetrahymena*. Partial chicken ovalbumin was also successfully expressed in *Tetrahymena* by Gaertig et al. (WO 00/46381). Selection occurred in both cases with Paclitaxel (TAXOL®). This system developed by Gaertig et al. has a patent pending (WO 00/46381).

Integration of the heterologous gene by homologous DNA recombination is possible in *Tetrahymena*. Mitotically stable transformants can be generated by this. Targeted gene knockouts are also possible by homologous DNA recombination (Bruns & Cassidy-Hanley in: Methods in Cell Biology, Volume 62, Ed. Asai & Forney, Academic Press (1999) 501–512); Hai et al. in: Methods in Cell Biology, Volume 62, Ed. Asai & Forney, Academic Press (1999) 514–531; Gaertig et al. (1999) Nature Biotech. 17: 462–465 or Cassidy-Hanley et al. 1997 Genetics 146: 135–147). In addition, the somatic macronucleus or the generative micronucleus can be transformed in alternation. During macronucleus transformation, sterile transformants are obtained, which can be advantageous relative to safety or acceptance questions.

In view of the prior art, it was now the task of the present invention to furnish a new production method that is simple and economical to carry out for human proteins that offers the possibility of post-translational protein modifications, corresponding as much as possible to the base type of different human modifications, and also advantageously permit secretion of the recombinant proteins, preferably dispensing with the use of non-human secretion signals (secretion sequences).

This and additional tasks not explicitly mentioned that can easily be deduced from the relations discussed in the introduction or concluded from them are solved by the variants of the present invention defined in the patent claims.

A method for production of recombinant human proteins can be made available in surprisingly simple fashion by transforming *Tetrahymena* cells with recombinant DNA containing at least one functional gene that codes for human protein, culturing the recombinant *Tetrahymena* cells, in which the gene that codes for the human protein is expressed, and then isolating the proteins. The recombinant human proteins produced in this way have simple glycosylation patterns whose structures are much more similar to those of mammal cells than those of yeasts. On the other hand, the cultivation and growth properties correspond more to those of yeast, i.e., rapid growth on inexpensive media, which can be achieved without excessive technical demands.

A preferred species of the genus *Tetrahymena* according to the invention is *Tetrahymena thermophila*.

Human protein is understood to mean, according to the invention, a protein for which a corresponding coding DNA sequence can be isolated from humans. The DNA sequence ultimately used for recombinant expression need not be isolated from human cells, but can instead be present in modified form or be produced artificially. The produced protein can also have mutations, like deletions, replacement of certain amino acids, etc., relative to the protein that can be isolated from human cells. In particular, human proteins according to the invention mean human proteins for therapeutic use, like cytokines (interferons, interleukins), enzymes, hormones (insulin, EPO, growth hormones), blood factors (factor VIII, factor IX) and others.

Simple glycosylation patterns are understood for the purpose of the present invention to mean mostly glycosylation patterns of the base structure GlcNAc2-Man2-5.

Functional gene, for the purposes of the present invention, is understood to mean the gene that can be expressed in the target organism. In particular, a functional gene therefore includes, in addition to a coding sequence, a promoter that is functional in the target organism that leads to transcription of the coding sequence. A functional promoter of this type can have, among other things, one or more TATA boxes, CCAAT boxes, GC boxes or enhancer sequences. The functional gene could also include a terminator that is functional in the target organism that leads to interruption in transcription and contains signal sequences that lead to polyadenylation of mRNA. The coding sequence of the functional gene also has all the properties necessary for translation in the target organism (for example, start codon (for example, ATG), stop codon (TGA), A-rich region before the start (translation initiation site), Kozak sequences, poly-A site. The gene can also have the codon usages specific for *Tetrahymena* (Wuitschick & Karrer, J. Eukaryot. Microbiol. (1999)).

In a preferred variant of the present invention, the gene being expressed is a gene for human serum albumin (HSA), or a variant of it. The produced protein is therefore preferably human serum albumin.

A variant of recombinant HSA is understood to mean, according to the invention, a gene with at least 70%, preferably 80%, especially 90%, and quite especially 95%, homology to the sequence of the gene for human serum albumin (HSA). In particular, a probe of In particular, a probe of preferably 100 to 300 bp, selected from the sequence of the gene for human serum albumin (HSA) under standard hybridization conditions hybridizes on a variant of this gene.

In the present work, successful expression of recombinant HSA in *Tetrahymena* is described for this first time and therefore it is the first time that a human protein could be successfully expressed in *Tetrahymena*.

For this purpose, the full coding sequence of HSA, including the leader sequence, was amplified by PCR and ligated in a *Tetrahymena* expression vector (see example 2). After transformation of *Tetrahymena* with this construct and selection of the transformants for taxol resistance (see example 3), cultures were run in skim milk medium with addition of protease inhibitor (see example 5). Proteins secreted into the medium by *Tetrahymena* were separated by SDS-PAGE and HSA was detected in a Western Blot with an HSA-specific antibody (see FIG. 2). Surprisingly, it was possible not only to produce the recombinant HSA, but also secrete it into the medium.

Contrary to all expectations, the human leader sequence proved to be fully functional in *Tetrahymena*.

*Tetrahymena* cells that secrete the expressed protein form a preferred variant of the present invention. Isolation of the proteins can occur in this variant from the culture supernatant.

An especially preferred variant of the present invention therefore concerns methods for production of recombinant human protein, in which the gene coding for the human protein includes a human leader sequence that causes secretion of the expressed proteins by *Tetrahymena*. See, for example, Stryer, L., Biochemie, $4^{th}$ Edition, Spektrum Akademischer Verlag, 1996, pages 802–3, or Alberts, B. et al., Molecular Biology of the Cell, $3^{rd}$ Edition, Garland Publishing, New York and London, 1994, Chapter 12 or Lodish, H. et al., Molecular Cell Biology, $4^{th}$ Edition, W H Freeman & Co. New York, 1999, Chapter 17, for a description of leader sequences (synonym of signal sequences) or leader peptides (or signal peptides). The leader sequence with particular preference includes the nucleotide sequence atgaagtggg taacctttat ttcccttctt tttctcttta gctcggctta ttcc (SEQ ID NO:5) or codes for a leader peptide containing the amino acid sequence Met Lys Trp Val Thr Phe Ile Ser Leu Leu Phe Leu Phe Ser Ser Ala Tyr Ser (SEQ ID NO:6). In another preferred variant, the leader sequence includes a sequence corresponding to the propeptide sequence agggtgt-gtttcgtcga (SEQ ID NO:7), or codes for a propeptide containing the amino acid sequence Arg Gly Val Phe Arg Arg (SEQ ID NO:8).

In another variant of the present invention, the human protein is expressed on the surface of the recombinant *Tetrahymena* cells.

Another variant of the present invention concerns recombinant *Tetrahymena* cells containing DNA that codes for human protein. The recombinant *Tetrahymena* cells preferably express the recombinant human gene. The expressed gene with particular preference includes a human leader sequence. Said leader sequence preferably includes SEQ ID NO:5 or codes for a leader peptide containing SEQ ID NO:6. In another preferred variant, the leader sequence contains a sequence corresponding to propeptide sequence SEQ ID NO:7 or codes for a propeptide containing SEQ ID NO:7.

With particular preference, the recombinant *Tetrahymena* cells secrete the recombinant human protein. In a preferred variant, the protein expressed and secreted in this way is a human serum albumin, or a variant of it.

Another variant of the present invention concerns a recombinant human protein, characterized by the fact that it has glycosylation patterns typical for *Tetrahymena*.

An expression vector for expression of human proteins in *Tetrahymena*, including a human leader sequence, forms another variant of the present invention. Expression vector is understood, according to the invention, to mean a nucleic acid molecule, like DNA or RNA, circular or linear, for example, a plasmid, a cosmid or an artificial chromosome that makes it possible to incorporate a recombinant gene in the host cell and express the gene in the cell. The vector can be present episomally in the cell, i.e., be self-replicating or be integrated into the genome of the host cell. Integration can occur randomly, or also by homologous recombination. In addition to the recombinant gene being expressed, such an expression vector according to the invention can also include other sequences helpful for the task, like multiple cloning sites, autonomously replicating sequences, marker genes for the host and all necessary sequences, in order to permit replication in *E. coli* for cloning purposes, like an ori, *E. coli*-specific marker, etc.

Successful expression of a human protein in *Tetrahymena* is described for the first time in the present work.

Mannose-rich type with 5–9 mannose and 2 GlcNAc residues

Simple base structure: with 2–5 mannose and 2 GlcNAc residues

Complex type: with galactose, fucose and sialic acid residues (N-acetyl neuraminic acid)

Yeast N-glycans consist exclusively of a mannose-rich type with 8–50 mannose residues The plant complex type has no sialic acid, but can possess xylose residues (allergenic potential).

Figure 1:
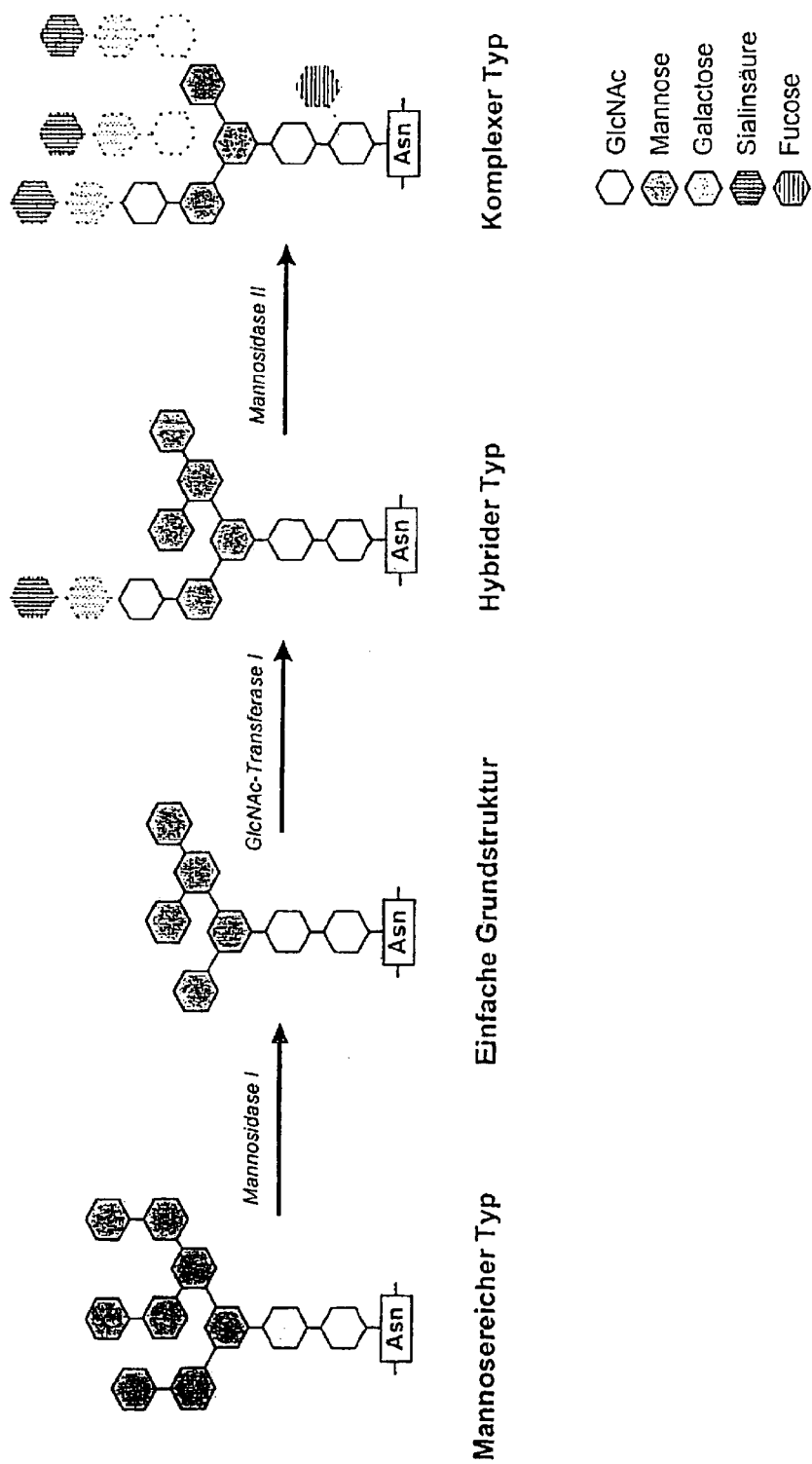
FIG. 1: N-bonded protein glycosylation
Figure 2:
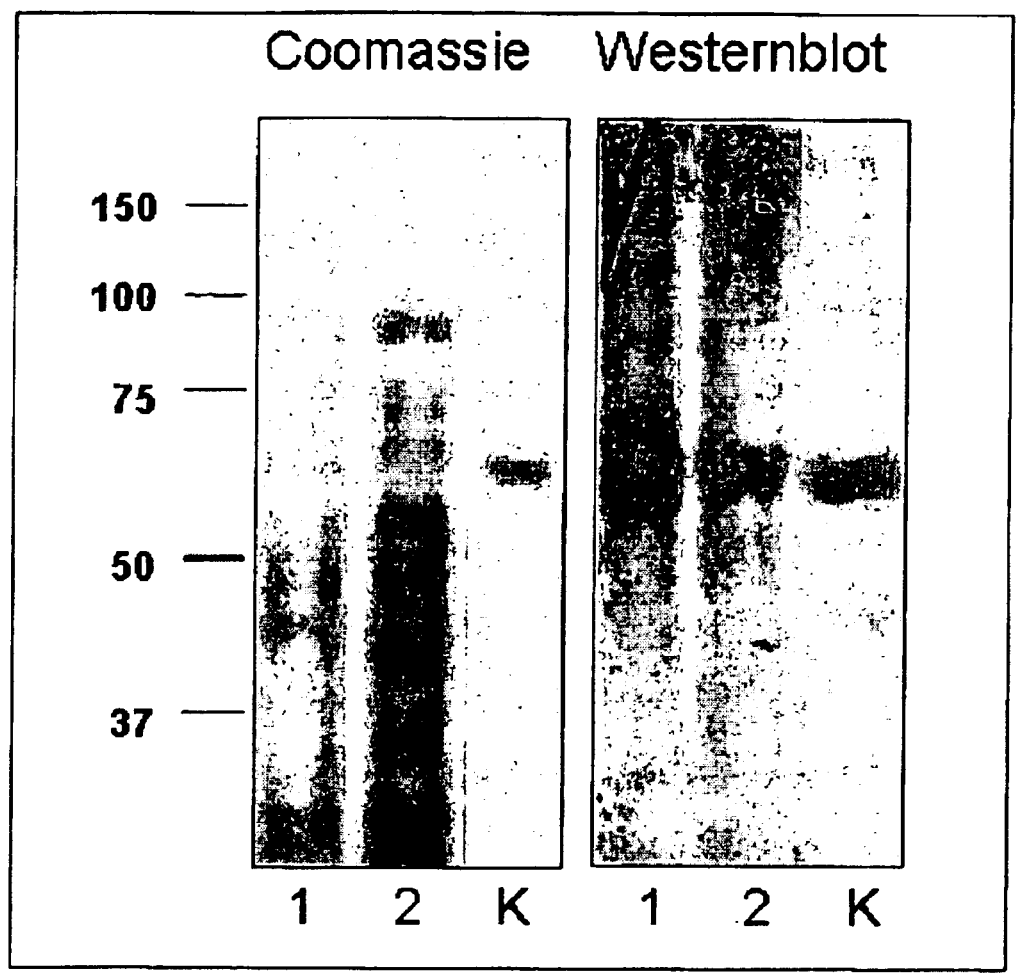

FIG. 2: Expression of HSA in *Tetrahymena*

Track 1 and 2: media fraction of *Tetrahymena*, transformed with pBHSA after 24 and 48 hours, track K: natural HSA of control. SDS-PAGE, stained with Coomassie blue and Western Blot with HSA antibodies and secondary antibodies (coupled to alkaline phosphatase).

EXAMPLES

The following examples serve to explain the invention without limiting the invention to these examples.

Example 1

Organisms and Culturing Conditions

*Tetrahymena thermophila* (strains B1868 VIII, B2086 II, B*VI, CU428, CU427, CU522, made available by J. Gaertig, University of Georgia, Athens, Ga., USA) was cultured in modified SPP medium (2% proteospeptone, 0.1% yeast extract, 0.2% glucose, 0.003% Fe-EDTA (Gaertig et al. (1994) PNAS 91: 4549–4553)) and skim milk medium (2% skim milk powder, 0.5% yeast extract, 1% glucose, 0.003% Fe-EDTA or MYD medium (2% skim milk powder, 0.1% yeast extract, 0.2% glucose, 0.003% FE-EDTA)) with addition of antibiotic solution (100 U/mL penicillin, 100 µg/mL streptomycin and 0.25 µg/mL amphotericin B (SPPA medium)) at 30° C. in 50 mL volumes in 250 mL Erlenmeyer flasks during shaking (150 rpm).

Plasmids and phages were multiplied and selected in *E. coli* XL1-Blue, MRF', TOP10F' or JM109 (Stratagene, Invitrogen, GibcoBRL Life Technologies). Culturing of the bacteria occurred under standard conditions in LB or NZY medium with antibiotics in standard concentrations (Sambrook et al. (1989) Molecular Cloning: A Laboratory Manual, Cold Spring Harbor Laboratory, Cold Spring, N.Y.).

Example 2

Production of the Expression Construct pBHSA

The vector pBICH3 (Gaertig et al. 1999 Nature Biotech. 17: 462–465, WO 00/45381) contains the coding sequence of the Ichthyophthrius I antigen (G1) preprotein, flanked by the non-coding, regulatory sequences of *Tetrahymena thermophila* BTU1 gene. A modified plasmid (pBICH3-Nsi) with an Nsi I cleavage site at the start (furnished by J. Gaertig, University of Georgia, Athens, Ga., U.S.A) was used, in order to produce the human serum albumin (HSA) expression construct pBHSA. For this purpose, Nsi I and Bam HI cleavage sites were inserted by PCR at the start and stop of the coding HSA sequence. An isolated plasmid that contains the complete cDNA sequence of HSA was used for PCR as template. The primer HSA-Nsi-1
5'-GGCACAATGCATTGGGTAACCTTTATTAGC-3' (SEQ ID no. 1) and HSA-Bam-R
5'-AAATGGGATCCTCATAAGCCTAAGGCAGCTT GAC-3' (SEQ ID no 2)

produced the PCR product that contains the complete coding sequence of HSA, flanked by Nsi I and Bam HI cleavage sites. The PCR product and the plasmid pBICH3-Nsi were cleaved with the restriction enzymes Nsi I and Bam HI, purified with agarose gel and ligated. The expression construct pBHSA so produced contains the complete HSA coding sequence inserted in the correct reading frame in the regulatory sequences of BTU1 gene. For transformation of *Tetrahymena*, this construct was linearized by digestion with the restriction enzymes Sac II and Xho I.

During a successful transformation, the BTU1 gene was replaced by this construct by homologous recombination, so that resistance of the cells to Paclitaxel was produced.

Example 3

Macronucleus Transformation of *Tetrahymena* with pBHSA $5 \times 10^6$ *Tetrahymena thermophila* cells (CU522) were used for transformation. Culturing of the cells occurred in 50 mL SPPA medium at 30° C. and at 250 mL Erlenmeyer flasks on a rocking device at 150 rpm to a cell density of about $3–5 \times 10^5$ cells/mL. After centrifuging (1200 g) for 5 minutes, the cells were pelletized and the cell pellet was resuspended in 50 mL 10 mM TRIS-HCL (hydroxymethyl) aminomethane hydrochloride (pH 7.5) and centrifuged as before. This washing step was repeated and the cells resuspended in 10 mM TRIS-HCL (pH 7.5, plus antibiotic) at a cell density of $3 \times 10^5$ cells/mL, transferred to a 250 mL Erlenmeyer flask and incubated for 16–10 hours without shaking at 30° C. (hunger phase). After the hunger phase, the cell count was determined again, centrifuged as above and the cells adjusted to a concentration of $5 \times 10^6$ cells/mL with 10 mM TRIS-HCL (pH 7.5). 1 mL of the cell suspension was used for the transformation. The transformation occurred with microparticle bombardment (see below). For regeneration, the cells were taken up in SSPA medium and incubated at 30° C. without shaking in Erlenmeyer flasks. After 3 hours, Paclitaxel was added in a final concentration of 20 µm and the cells transferred in aliquots of 100 µL to 96-well microtiter plates. The cells were incubated in a moist, darkened box at 30° C. After 2–3 days, Paclitaxel resistance clones could be identified. Positive clones were reinoculated in fresh medium with 25 µm Paclitaxel. By culturing of the cells in an increasing Paclitaxel concentration (to 80 µm, a complete "phenotypic assortment" (Gaertig & Kapler (1999)) was reached.

For analysis of the clones, about 4 mL of the cultures in SPPA were cultured with Paclitaxel, the DNA isolated (Jacek Gaertig et al. (1994) PNAS 91: 4549–4553) and the DNA integrated in the BTU1 locus, amplified by PCR. The BTU1-specific primer BTU1-5'F (AAAAATAAAAAAGTTTGAAAAAAAACCTTC (SEQ ID no. 3), served as primer about 50 bp before the start codon and BTU1-3R' (GTTTAGCTGACCGATTCAGTTC (SEQ ID no. 4)), 3 bp after the stop codon. The PCR products were analyzed uncleaved and cleaved on a 1% agarose gel with Hind III, Sac I or Pst I. The complete "phenotypic assortment" was checked via RT-PCR with the BTU1-specific primers (Gaertig & Kapler (1999)).

Example 4

BIOLISTIC Transformation (Microparticle Bombardment)

Transformation of *Tetrahymena thermophila* occurred with BIOLISTIC transformation, as described in Burns & Cassidy-Hanley (Methods in Cell Biology, Volume 62 (1999) 501–512); Gaertig et al. 91999) Nature Biotech. 17: 462–465) or Cassidy-Hanley et al. (1997 Genetics 146: 135–147)). Handling of the BIOLISTIC PDS-1000/He Particle Delivery System (BIO-RAD) is described in detail in the corresponding handbook.

For transformation, 6 mg gold particles (0.6 µm; BIO-RAD) were loaded with 10 µg linearized plasmid DNA (Sanford et al. (199) Biotechniques 3:3–16; Bruns & Cassidy-Hanley (1999) Methods in Cell Biology, Volume 62: 501–512).

Preparation of the gold particles: 60 mg of 0.6 µm gold particles (BIO-RAD) were resuspended in 1 mL ethanol. For this purpose, the particles were vigorously mixed 3 times every 1–2 minutes on a vortex. The particles were then centrifuged for 1 minute (10,000 g) and the supernatant carefully taken off with a pipette. The gold particles were resuspended in 1 mL sterile water and centrifuged as above. This washing step was repeated once, the particles resuspended in 1 mL 50% glycerol and stored at −20° C. in aliquots of 100 µL.

Preparation of transformation: the macrocarrier holder, macrocarrier and stop screens were placed for several hours in 100% ethanol and the rupture disks in isopropanol. A macrocarrier was then inserted into the macrocarrier holder and dried in air.

Loading of the gold particles with DNA: all work occurred at 4° C. Gold particles, prepared vector, 2.5 M CaCl$_2$, 1 M spermidine, 70% and 100% ethanol were cooled on ice. 10 µL of the linearized vector DNA (1 µg/mL) was added to 100 µL of the prepared gold particles and carefully vortexed for 10 seconds. 100 µL 2.5 M CaCl$_2$ was first added, vortexed for 10 seconds and then 40 µL of 1 M spermidine added and vortexed carefully for 10 minutes. After addition of 200 µL 70% ethanol, the particles were vortexed for 1 minute and then centrifuged for 1 minute at 10,000 g. The pellet was resuspended in 20 µL 100% ethanol, centrifuged and then resuspended in 35 µL 100% ethanol.

The particles so prepared were carefully introduced to the center of a macrocarrier with a pipette. The macrocarrier was then placed in a box of hygroscopic silica gel for transformation.

Transformation: 1 mL of the prepared cells (see above) was introduced into the center of a round filter, moistened with 10 mM tris-HCl (pH 7.5) in a petri dish and introduced into the lowermost insertion strip of the transformation chamber of the BIOLISTIC PDS-1000/He Particle Delivery System. Transformation occurred with the prepared gold particles at a pressure of 900 psi (two 450 psi rupture disks) and a vacuum of 27 inches Hg in the transformation chamber. The cells were then immediately transferred to Erlenmeyer flasks with 50 mL SPPA medium and incubated at 30° C. without shaking.

Example 5

Expression of HSA in *Tetrahymena*

Cultures in Erlenmeyer flasks in 20 mL skim milk medium with addition of protease inhibitor (complete, EDTA-free protease inhibitors—cocktail tablets, Roche Diagnostics GmbH) were cultured from positive transformants and as control from untransformed *Tetrahymena* wild type cells. After 24 h and 48 h (at a cell density of about 1×10$^6$ cells/mL), the cells were centrifuged and the residue of the supernatant mixed with 1/10 volumes of ice cold TCA and incubated on ice for 30 minutes and then centrifuged for 30 minutes at 4° C. and maximum rpm. The pellet was washed with 300 µL ice cold acetone and centrifuged for 5 minutes at 4° C. at maximum rpm. The supernatant was taken off, the pellet dried (vacuum), resuspended in 150 µL sample buffer and incubated for 10 minutes at 95° C. The proteins so recovered from the media fraction, the proteins secreted by *Tetrahymena* into the medium were separated according to standard methods by SDS-PAGE and HSA detected with an HSA-specific antibody (Sigma) in the Western Blot (see FIG. 2). Natural HSA (Sigma) was used as positive control.

What is claimed is:

1. Method for production of recombinant human proteins in *Tetrahymena*, comprising the steps:
   a) transforming said *Tetrahymena* cells with recombinant DNA containing at least one functional gene that codes for said recombinant human protein, said gene comprises a DNA sequence encoding a human leader sequence;
   b) culturing said transformed *Tetrahymena* cells and expressing said gene; and
   c) isolation said human protein.

2. The method for production of a recombinant human protein according to claim 1, wherein said *Tetrahymena* cells secrete said human protein.

3. The method for production of a recombinant human protein according to claim 1, wherein said *Tetrahymena* cells express said human protein on their surface.

4. The method for production of a recombinant human proteins according to claim 2, wherein said human protein is isolated from a culture supernatant.

5. The method for production of a recombinant human protein according to claim 1, wherein said human leader sequence leads to secretion of said human protein by *Tetrahymena*.

6. The method for production of a recombinant human protein according to claim 1, wherein said expressed gene codes for human serum albumin (HSA).

7. The method for production of a recombinant human protein according to claim 1, wherein said human protein is human serum albumin.

8. A recombinant *Tetrahymena* cell comprising a recombinant DNA containing at least one functional gene that codes a recombinant human protein, and said gene further comprises a DNA sequence encoding a human leader sequence.

9. The recombinant *Tetrahymena* cells according to claim 8, wherein said cells express a recombinant human gene.

10. The recombinant *Tetrahymena* cells according to claim 9, in wherein said expressed gene comprises a DNA sequence encoding a human leader sequence.

11. The recombinant *Tetrahymena* cells according to claim 9, wherein said expressed gene codes for human serum albumin.

12. The recombinant *Tetrahymena* cells according to claim 9, wherein said cells secrete a recombinant human protein.

13. The recombinant *Tetrahymena* cells according to claim 12, wherein said secreted human protein is human serum albumin.

14. An expression vector for expression of human proteins in *Tetrahymena*, containing a human leader sequence.

* * * * *